United States Patent [19]

Jowett

[11] 4,166,805

[45] Sep. 4, 1979

[54] RANEY CATALYSTS

[76] Inventor: Peter Jowett, Rivington, 33 Strines Rd., Marple, Cheshire, England, SK6 7DT

[21] Appl. No.: 798,541

[22] Filed: May 19, 1977

[51] Int. Cl.² .................... B01J 25/00; B01J 25/02; B01J 31/02
[52] U.S. Cl. .................... 252/430; 252/477 Q
[58] Field of Search ............ 252/430, 477 Q

[56] References Cited

U.S. PATENT DOCUMENTS

| | | | |
|---|---|---|---|
| 2,205,552 | 6/1940 | Arnold | 252/430 X |
| 2,730,533 | 1/1956 | Umhoefer | 252/430 X |
| 3,544,485 | 12/1970 | Taira et al. | 252/477 Q |
| 3,691,103 | 9/1972 | Csuros et al. | 252/477 Q |

*Primary Examiner*—W. J. Shine
*Attorney, Agent, or Firm*—Sughrue, Rothwell, Mion, Zinn and Macpeak

[57] ABSTRACT

The invention relates to a hydrogenation catalyst which comprises a Raney metal catalyst dispersed in an aliphatic primary, secondary or tertiary amine, a diamine or a cyclic amine which has at least one chain of 8 to 22 carbon atoms, or a salt of such an amine or diamine.

17 Claims, No Drawings

RANEY CATALYSTS

The present invention relates to catalysts of the type known as Raney Catalysts.

Raney Catalysts such as Raney Nickel and Raney Cobalt are well known and extensively used for the hydrogenation of carbon-carbon unsaturated bonds, nitriles to amines, nitro compounds to amines and for many other hydrogenation reactions. Such catalysts are generally prepared by the digestion with a strong alkali of an alloy of aluminium and a metal active for hydrogenation. The aluminium reacts with the alkali, generally sodium hydroxide, with the evolution of hydrogen and after washing of the remaining metal there remains a finely divided metal powder of high surface area having adsorbed hydrogen.

A number of disadvantages are associated with Raney Catalysts produced by digestion of a catalytic metal/aluminum alloy with a strong alkali which tend to restrict their use and of these the principle disadvantage is that the catalyst is pyrophoric in the dry state.

Therefore, for safety reasons, Raney Catalysts are supplied, transported and used immersed in water. However, even in this protected state there are a number of disadvantages associated with the use of Raney Catalysts.

Firstly, the Raney Catalyst wetted and dispersed in water is not dispersible in nor wetted by oily materials such as organic nitriles, glyceride oils and other water insoluble materials which are commonly the raw materials to be hydrogenated. This defect results in difficulties in introducing the catalyst into hydrogenation equipment and also a slow rate of hydrogenation even in well designed equipment.

Secondly, the immersed Raney Catalyst is hazardous to manipulate since spillages during manufacture, transport or use allows the protective water to evaporate thus leaving pyrophoric nickel as a fire hazard. This disadvantage is of course particularly acute where there is a chance of the catalyst/water mixture spilling onto the clothing of personnel engaged in its handling.

Various attempts have been made to overcome the disadvantage of non-oil wettability by replacing the protective water medium by an organic solvent. Such products are somewhat easier to use from the point of view of wettability with the reactant but are either even more hazardous from an inflammatory point of view or are of reduced activity for hydrogenation.

It is therefore an object of the present invention to provide a Raney Catalyst in which the above mentioned disadvantage are obviated or mitigated.

According to the present invention there is provided a hydrogenation catalyst comprising a Raney Catalyst active for hydrogenation dispersed in an aliphatic primary, secondary or tertiary amine, a cyclic amine or a diamine, said amine or diamine having at least one chain of 8 to 22 carbon atoms, or a salt of such an amine or diamine, and said hydrogenation catalyst having been prepared by blending the amine or diamine, or salt thereof, with the Raney Catalyst.

The Raney Catalysts which may be used for formulating the hydrogenation catalyst of the invention may, for example, be selected from Raney Nickel, Raney Cobalt, Raney Copper and Raney Iron. As stated previously, these catalysts are generally prepared by reacting an alloy of aluminium and the appropriate metal with an alkaline solution, usually a solution of a strong alkali such as sodium or potassium hydroxide.

If it is desired, the Raney Catalyst may contain a trace of a promoter, such as nickel cobalt, zirconium, chromium, molybdenum, iron, copper, silver and palladium for increasing its hydrogenation activity, the promoter generally being used in an amount of up to 10% based on the weight of the Raney Catalyst.

The Raney Catalyst used for formulating the hydrogenation catalyst of the invention must of course be one which is active for hydrogenation. It is therefore preferred that the Raney Catalyst used is one which has not previously been used for a hydrogenation reaction, although it is possible to use a regenerated catalyst. The formulated hydrogenation catalyst may of course be used for hydrogenation until its activity becomes too low.

The amines which may be used for formulating the catalyst of the invention all contain at least one saturated or unsaturated, straight or branched carbon chain of 8 to 22 carbon atoms and are primary, secondary or tertiary amines, diamines, preferably aliphatic diamines, or cyclic amines. Salts of the aforementioned amines or diamines may also be used.

The amine may be of synthetic manufacture and a suitable example of such a product is available under the name SYNPROLAM.

For commercial reasons however it is preferred that the amines, diamines and salts used are at least partially derived from readily available natural products such as animal tallow, rape seed oil, coco oil, soya bean oil and fish oils.

The amines are generally obtained from the natural product by hydrolysis of the tri-glyceride esters in the product to liberate various $C_8$-$C_{22}$ fatty acids and subsequent conversion of the acid mixture by known methods to give amines in which the carbon chains have the same number of carbon atoms as the precursor acid. Depending on the process used for the conversion of the acid, there may be obtained a mixture of primary amines or a mixture of secondary or tertiary amines, each amine possibly having more than one type of $C_{8-22}$ carbon chain.

Such an amine mixture is well suited for formulating the catalyst of the invention since it possesses all of the necessary properties and separation of the component amines is not required.

The diamines which may be used may be derived from a lower alkylene diamine, e.g. ethylene diamine or propylene diamine, to at least one nitrogen of which is attached a $C_8$-$C_{22}$ chain.

The cyclic amines are those having at least one nitrogen atom in a heterocyclic ring and at least one $C_8$-$C_{22}$ chain attached either to a ring nitrogen atom or a ring carbon atom. A particularly preferred example of cyclic amine for use in the invention is an imidazoline substituted at the 2-position with a $C_8$-$C_{22}$ carbon chain.

The amine or diamine salts which may be used are preferably addition salts of the amine or diamine with a carboxylic acid such as acetic acid or oleic acid.

To prepare the hydrogenation catalyst of the invention, it is preferred that the amine, diamine or salt is mixed with finely divided Raney Catalyst which, for safety, should be protected under water. The amine, diamine or salt behaves as a cationic surface active agent and forms a layer around each of the catalyst particles, thus displacing the water, and there is formed a dispersion of catalyst particles in the amine, diamine or salt. The displaced water may separate out from the catalyst/amine dispersion as a separate layer so that it may be easily decanted. Alternatively, the water may remain in the dispersion in dispersed, dissolved or emulsified form and, if this is the case, the amount of water may vary between a trace and 95% by weight of the finished product.

The amount of amine, diamine or salt to be included in the hydrogenation catalyst of the invention depends to a large extent on the intended final use of the catalyst but is preferably from 5 to 95% by weight based on the weight of the finished product and is more preferably from 5 to 95% based on the weight of nickel.

The hydrogenation catalyst produced has a consistency varying between that of a fluid paste and a waxy substance depending on the amounts of the various ingredients used and also on the type of amine, diamine or salt. Packaging used for the catalyst depends on its consistency and in certain cases it is possible to flake the catalyst so that it may be provided in sacks for ease of handling.

It is also possible to include materials other than the Raney Catalyst and amine, diamine or salt into the hydrogenation catalyst. Such other materials include the product to be hydrogenated, material chemically similar to the product of hydrogenation, aliphatic carboxylic acid, aliphatic nitriles such as fatty nitriles, aliphatic triglyceride oils, aliphatic alcohols, aliphatic esters or aliphatic hydrocarbons.

Additionally or alternatively the hydrogenation catalyst of the invention may also include processing aids such as a filter aid or decolourising charcoal.

The hydrogenation catalyst of the invention has the following advantages.

1. The product is immediately and completely wetted by all organic and oily materials into which it comes into contact and it is extremely convenient to use for all hydrogenations of organic materials.

2. It is completely safe during storage, in distribution, and in use, and is covered by a non-volatile protective material at all times.

3. It is readily prepared and manufactured from conventional Raney Nickel initially wetted and dispersed in water, without necessarily prior removal of all the water which has advantages for nitrile to amine hydrogenations, as known by those skilled in the art.

The invention will now be further described by way of example only with reference to the following examples.

In the examples, the hydrogenation catalyst was prepared from the ingredients specified by mixing in a planetary, Z-bladed or other suitable mixing apparatus.

EXAMPLE I 100 kilograms of Raney Nickel consisting of 60 kilograms of nickel wetted with and immersed in 40 kilograms of water was introduced into a mixer and to this was added, whilst undergoing agitation, 25 kilograms of a distilled primary amine with an aliphatic chain length distribution similar to that obtained in animal tallow $C_{16}$-palmitic, $C_{18}$-oleic stearic, maintained at 80° C. The primary amine rapidly and preferentially wetted out the nickel particles, displacing water from the nickel particles, and the displaced water subsequently was rapidly emulsified within the fatty amine protective material. When a uniform mixture had been obtained, the product was removed and introduced into suitable containers.

EXAMPLE II

The procedure of Example I was followed except that 15 kilograms of the distilled primary amine was used. When the primary amine had wetted out the nickel particles, displacing the water from them and emulsifying the water in the fatty amine protective material, and a uniform mixture had been obtained, 15 kilograms of a fatty nitrile maintained at 70° C. was added and mixed with the hydrogenation catalyst. When a uniform mixture had been obtained the product was introduced into suitable containers.

EXAMPLE III

The procedure of Example I was followed except that 15 kilograms of the amine was used. When the primary amine had wetted out the nickel particles, displacing the water from them and emulsifying the water in the fatty amine protective material, and a uniform mixture had been obtained, 10 kilograms of decolourising charcoal was added and mixed with the nickel in amine paste. When a uniform mixture had been obtained the product was removed from the mixer and introduced into suitable containers.

The product of Examples I to III had the characteristics, at ambient temperature, of a paste which could be manipulated for indefinite periods in the presence of air with complete safety, and which could be rapidly dispersed in aliphatic nitriles, glyceride oils or other oily materials for easy introduction into hydrogenation plant and equipment.

The following Examples further illustrate the hydrogenation catalyst of the invention.

EXAMPLE IV 100 g. of Raney Nickel consisting of 60 g. Nickel wetted with and immersed in 40 g. water was agitated as described in Examples I to III, and 25 g. of undistilled primary tallow amine at 80° C. added. The resultant mix had similar appearance and properties to those of the product from Example I, in which a distilled tallow amine was used.

EXAMPLE V

In a repeat of Example IV, the primary tallow amine was added at a temperature of 90° C. Much of the displaced water remained as a separate phase and when the mixture had cooled this water could be decanted off to leave a somewhat stiffer paste than the products from Examples I and IV.

EXAMPLE VI

In a repeat of Example IV the tallow amine was replaced by a primary amine (25 g) based on the oleic chain length distribution. The amine was added at a temperature of 80° C. to the Raney Nickel, wetted with and immersed in water. In this case much of the displaced water remained as a separate phase and could be decanted away from the product paste after cooling.

EXAMPLE VII

In a repeat of Example VI the primary amine based on the oleic chain length distribution was added at 20° C. Again much of the displaced water remained as a separate phase which could be decanted away from the product.

EXAMPLE VIII

In a repeat of Example IV the tallow amine was replaced by a primary amine based on coco chain length distribution. In this case part of the displaced water separated out as a separate phase which could be decanted away from the product both before and after cooling down to ambient temperature.

EXAMPLE IX

In a repeat of Example IV, a primary amine based on the C12 aliphatic carboxylic acid (lauric acid) was used in place of the primary tallow amine. In this case a small amount of the displaced water separated out and could be decanted away from the product.

EXAMPLE X

In a repeat of Example IV, a primary amine based on the fully hydrogenated tallow chain length distribution was used in place of the primary tallow amine. In this case the displaced water rapidly emulsified into the product or became entrained in the product to give a firm paste when cooled to room temperature. When a portion of the product was heated to 100° C. some of the entrained water separated out to form a separate phase which could be separated off.

EXAMPLE XI

In a repeat of Example IV, the primary amine based on the tallow chain length distribution was replaced by a mixture of equal parts by weight of the primary amine based on the tallow chain length distribution and the primary amine based on the hydrogenated tallow chain length distribution. Again the displaced water rapidly emulsified into the product or became entrained in the product to give a firm paste when cooled to room temperature.

EXAMPLE XII

In a repeat of Example IV the primary amine based on the tallow chain length distribution was replaced by an equal weight of the secondary amine containing two long chain alkyl groups with the hydrogenated rape seed fatty acid chain length distribution. At least one of the long chain alkyl groups in the secondary amine is $C_{22}$ (saturated) or $C_{20}$ (saturated). The displaced water rapidly emulsified into the product or became entrained in the product to give a firm paste when cooled to room temperature.

EXAMPLE XIII

In a repeat of Example IV the primary amine based on the tallow chain length distribution was replaced by an equal weight of the tertiary amine containing one methyl group and two alkyl groups with the hydrogenation tallow chain length distribution, (i.e. each tertiary amine contains at least one $C_{16}$ or $C_{18}$ group). The displaced water rapidly emulsified into the product or became entrained in the product to give a hard paste when cooled to room temperature.

EXAMPLE XIV

In a repeat of Example IV the primary tallow amine was replaced by an equal weight of a diamine of the N-alkyl propylene diamine type wherein the alkyl group had the tallow chain length distribution. The displaced water emulsified into the product to give a soft paste of homogenous appearance when cooled to room temperature.

EXAMPLE XV

In a repeat of Example XIV the diamine was replaced by another diamine of the N-alkyl propylene diamine type in which the alkyl group had the coco chain length distribution. Again the displaced water emulsified into the product to give a soft paste of homogeneous appearance when cooled to room temperature.

EXAMPLE XVI

In a repeat of Example XIV the N-tallow propylene diamine was replaced by an equal weight of the dioleate salt of this N-tallow propylene diamine. Again the displaced water emulsified into the product to give a soft paste of homogeneous appearance when cooled to room temperature.

EXAMPLE XVII

In a repeat of Example IV the primary tallow amine was replaced by an equal weight of an 2-alkyl-1-aminoethyl imidazoline wherein the alkyl group had the oleic chain length distribution. Again the displaced water emulsified into the product to give a soft paste of homogeneous appearance when cooled to room temperature.

EXAMPLE XVIII

In a repeat of Example IV the primary tallow amine was replaced by an equal weight of a 2-alkyl-1-hydroxyethyl imidazoline wherein the alkyl group had the oleic chain length distribution. Again the displaced water emulsified into the product to give a soft paste of homogeneous appearance when cooled to room temperature.

EXAMPLE XIX

In a repeat of Example XVIII the 2-alkyl-1-hydroxyethyl imidazoline, wherein the alkyl chain had the oleic chain length distribution, was mixed with the Raney Nickel/Water paste at 20° C. The displaced water emulsified into the product to give a soft paste similar in appearance and properties to the final product from Example XVIII.

EXAMPLE XX

In a repeat of Example IV, 100 g. of Raney Nickel/wetted with and immersed in water, consisting of 50 g. nickel and 50 g. water was taken and treated with 25 g. of undistilled primary tallow amine at 80° C. as described in Example IV. The displaced water emulsified into the product or became entrained in the product to give a soft paste from which some water drained on cooling to room temperature to leave a product similar in appearance and properties to the product from Example IV.

EXAMPLE XXI

In a repeat of Example IV 30 g. of standard bleaching earth was added slowly with continued agitation to the product obtained by mixing the Raney Nickel/water paste with primary tallow amine at 80° C. The resultant product when cooled to room temperature was an essentially free flow, non-pyrophoric powder.

EXAMPLE XXII

In a repeat of Example XXI in which the primary tallow amine at 80° C. was added to a mixture of the Raney Nickel of water paste and the standard bleaching earth, again an essentially free flow, non-pyrophoric powder was obtained. Care was required during the blending of the bleaching earth with the Raney Nickel/water paste since the bleaching earth had a high water absorption capacity.

EXAMPLE XXIII

In a repeat of Example IV, the primary tallow amine was replaced by the tertiary amine obtained by condensing the primary amine based on the soya chain length distribution with two molecules of ethylene oxide. This ethoxylated soya amine was added at 20° C. to the Raney Nickel/water mixture with agitation as previously. The displaced water rapidly emulsified into the product to give a soft non-pyrophoric paste from which only a small amount of water separated on storage.

EXAMPLE XXIV

In a repeat of Example IV, the Raney Nickel/water paste was replaced by a chromium promoted Raney Nickel, wetted with and immersed in water, obtained by digestion of a Raney Nickel/Aluminium alloy containing 2.5% Chromium, 47.5% Nickel and 50% aluminium, with caustic soda.

The displaced water emulsified with the product or became entrained in the product to give a final product of similar physical appearance to the product from Example IV.

EXAMPLE XXV

In a repeat of Example IV the Raney Nickel/water paste was replaced by Raney Cobalt similarly wetted with and immersed in water, obtained by digestion of a Raney cobalt alloy, containing 50% cobalt and 50% aluminium, with caustic soda. The displaced water emulsified into the product or became entrained in the product to give a final product of similar appearance to the product from Example IV.

EXAMPLE XXVI

In a repeat of Example 7 the primary amine based on the oleic chain length distribution was replaced by a synthetic (SYNPROLAM 35 from ICI) with an alkyl group containing approximately 70% $C_{13}$ and 30% $C_{15}$ chain length in which approximately 50% was mono-branched (mainly α-methyl). Addition of the amine at 20% gave a soft paste from which much of the displaced water could be decanted away.

To compare the activity of the hydrogenation catalyst of the invention with conventional Raney nickel under water a one liter stainless steel autoclave was charged with 600 g. of an aliphatic nitrile having a chain length distribution similar to that obtained in animal tallow. The nitrile was hydrogenated in separate experiments, at 140° C. under pressure of 500 psi in the presence of ammonia and of the catalyst of Example I and a conventional Raney nickel under water catalyst, there being two grams of nickel present in each experiment. The hydrogenation catalyst of the invention gave a 95% yield of primary amine in eight hours whereas the convention catalyst gave a 94% yield in fourteen hours.

It will therefore be seen that the hydrogenation rate using the hydrogenation catalyst of the invention is greatly increased compared to Raney nickel dispersed in water, based on similar proportions of nickel used.

What is claimed is:

1. A hydrogenation catalyst consisting essentially of Raney Catalyst pyrophoric in the dry state active for hydrogenation dispersed in an aliphatic primary, secondary or tertiary amine, a diamine or a cyclic amine, said amine or diamine having at least one chain of 8 to 22 carbon atoms, or a salt of such an amine or diamine, said hydrogenation catalyst having been prepared by blending the amine, diamine or salt with a mixture of said Raney Catalyst active for hydrogenation and water.

2. A hydrogenation catalyst as claimed in claim 1, wherein the Raney Catalyst is selected from Raney Nickel, Raney Cobalt, Raney Iron and Raney Copper.

3. A hydrogenation catalyst as claimed in claim 1, wherein the Raney Catalyst further contains a metallic promoter to increase the hydrogenation activity of said Raney Catalyst, wherein said metallic promoter is selected from nickel, cobalt, zirconium, chromium, molybdenum, copper, iron, silver and palladium.

4. A hydrogenation catalyst as claimed in claim 3, wherein the promoter is used in an amount of up to 10% by weight based on the weight of the Raney Catalyst.

5. A hydrogenation catalyst as claimed in claim 1, wherein the Raney Catalyst has not previously been used for hydrogenation.

6. A hydrogenation catalyst as claimed in claim 1, wherein the amine, diamine or salt is present in an amount of 5 to 95% by weight based on the weight of the finished product.

7. A hydrogenation catalyst as claimed in claim 1, wherein the amine, diamine or salt is produced at least partly from natural products.

8. A hydrogenation catalyst as claimed in claim 7, wherein the amine, diamine or salt has a chain length distribution corresponding to that in animal tallow, coco oil, soya oil, rape seed oil or fish oil.

9. A hydrogenation catalyst as claimed in claim 1, additionally containing water in dissolved, dispersed or emulsified form, the amount of water being between a trace and 95% by weight based on the weight of the finished product.

10. A hydrogenation catalyst as claimed in claim 1, wherein the amine, diamine or salt is in admixture with an aliphatic carboxylic acid, an aliphatic nitrile, an aliphatic triglyceride oil, an aliphatic alcohol, an aliphatic ester or an aliphatic hydrocarbon.

11. A hydrogenation catalyst as claimed in claim 1, wherein the amine, diamine or salt is in admixture with a material of the same chemical composition as the material to be hydrogenated during use of the catalyst or of the same chemical composition as the product of hydrogenation obtained by use of the catalyst.

12. A hydrogenation catalyst as claimed in claim 1, further comprising a processing aid.

13. A hydrogenation catalyst as claimed in claim 11, wherein the processing aid is a filter aid or de-colourising charcoal.

14. A hydrogenation catalyst as claimed in claim 1, wherein said Raney Catalyst active for hydrogenation is dispersed in the amine, diamine or salt in finely divided form, and said amine, diamine of salt behaves as a cationic surface active agent and forms a layer around each of the finely divided Raney Catalyst particles.

15. A hydrogenation catalyst as claimed in claim 14, wherein said amine, diamine or salt in forming a layer around each of the finely divided Raney Catalyst particles displaces water present.

16. A hydrogenation catalyst as claimed in claim 15, wherein said displaced water is separated out from the finely divided Raney Catalyst particle/amine, diamine or salt dispersion as a separate layer and decanted.

17. A hydrogenation catalyst as claimed in claim 1, wherein said amine is said cyclic amine.

* * * * *